US 7,850,783 B2

(12) United States Patent
Siegle et al.

(10) Patent No.: US 7,850,783 B2
(45) Date of Patent: Dec. 14, 2010

(54) METHOD AND APPARATUS FOR CLEANING HEARING AIDS

(75) Inventors: Gregory R. Siegle, Metairie, LA (US);
Roger P. Juneau, Destrehan, LA (US);
Edward J. Desporte, Covington, LA (US); Michael W. Major, Mandeville, LA (US); Gene Adoue, New Orleans, LA (US); Sherriel Lynn Johnson, Prairieville, LA (US); James David Moser, Orlando, FL (US); Brian M. Tanner, Destrehan, LA (US)

(73) Assignee: General Hearing Instrument, Inc., New Orleans, LA (US)

( * ) Notice: Subject to any disclaimer, the term of this patent is extended or adjusted under 35 U.S.C. 154(b) by 1163 days.

(21) Appl. No.: 11/427,769

(22) Filed: Jun. 29, 2006

(65) Prior Publication Data
US 2007/0022549 A1 Feb. 1, 2007

Related U.S. Application Data

(60) Provisional application No. 60/695,381, filed on Jun. 30, 2005.

(51) Int. Cl.
*B08B 9/027* (2006.01)
(52) U.S. Cl. .................... 134/22.1; 134/22.12
(58) Field of Classification Search ............. 134/22.1, 134/22.12, 22.13, 22.14, 22.16, 22.17, 22.18, 134/22.19, 23, 25.1, 25.4, 40, 42
See application file for complete search history.

(56) References Cited

U.S. PATENT DOCUMENTS

| 2,675,814 A | 4/1954 | Butler |
| 4,901,391 A | 2/1990 | Athalye |
| 4,953,215 A | 8/1990 | Weiss et al. |
| 5,196,657 A | 3/1993 | Jensen |
| 5,404,105 A | 4/1995 | Chari |
| 5,898,972 A | 5/1999 | Rademacher |
| 5,982,908 A | 11/1999 | Bauman |
| 2002/0126864 A1 | 9/2002 | Dennis, III et al. |
| 2003/0196687 A1 | 10/2003 | Campbell et al. |
| 2003/0198361 A1 | 10/2003 | Heerlein et al. |

*Primary Examiner*—Michael Kornakov
*Assistant Examiner*—Ryan Coleman
(74) *Attorney, Agent, or Firm*—Garvey, Smith, Nehrbass & North, L.L.C.; Seth M. Nehrbass; Charles C. Garvey, Jr.

(57) ABSTRACT

A method and apparatus for cleaning a hearing aid provides a housing having a motor drive and speed control. A rotary chamber is mounted to the housing and driven by the motor drive. A drive shaft can be provided connecting the motor drive and the rotary chamber. The rotary chamber has a wall with at least one receptacle for holding a hearing aid. The rotary chamber can have two openings, one for a hearing aid and a second opening for another hearing aid or a counterweight. The rotary chamber can be counterweighted to compensate for the weight of a single hearing aid or any other arrangements of multiple hearing aids. Each receptacle is configured to hold a hearing aid. The motor drive is powered sufficiently to rotate the hearing aid at the speed of between about 2800 and 3200 rpm in order to generate a G-force on the hearing aid of about 270 G's. Preferably, the motor drive rotates at a rotational speed sufficient to remove earwax, rotation lasting for a period of time of between about 5 and 45 (preferably 18-22) seconds.

17 Claims, 11 Drawing Sheets

METHOD AND APPARATUS FOR CLEANING HEARING AIDS

CROSS-REFERENCE TO RELATED APPLICATIONS

Priority of U.S. Provisional Patent Application Ser. No. 60/695,381, filed 30 Jun. 2005, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the removal of cerumen or earwax from a hearing aid. More particularly, the present invention relates to an improved method and apparatus for removing cerumen from hearing aids wherein a centrifuge arrangement rotates a chamber at a high rate of rotational speed, the chamber being specially configured to contain multiple hearing aids or a hearing aid and a counterweight that are in opposed, 180 degree apart positions.

2. General Background of the Invention

Hearing aid wearers are frequently presented with the problem of removing cerumen or earwax from a hearing aid. A hearing aid that becomes clogged with cerumen or earwax does not function properly.

Since the beginning of connecting electronic devices intended to transfer electro-acoustic energy directly to the human ear, the efficient, reliable performance, and the lifespan of these devices have been limited by cerumen buildup within key components.

These devices include hearing aids, tinnitus sound generators, delayed amplification devices used to manage stuttering, active hearing protectors, cellular phones, FM systems, and numerous other communication devices, The industries producing, the professionals dispensing, and the consumers using these products are in need of a novel cleaning system to effectively manage cerumen impaction.

Many products have been fabricated to manage cerumen impaction. These include heaters, suction pumps, vacuum domes, and wax removal screws In addition, desiccants have been developed to dry ear-worn devices in an effort to return them to normal operating specifications. Solvents have been developed to deodorize, disinfect, and free the foreign obstructions from devices.

These systems are in wide use in the hearing industry today, but they have all performed with less than optimum results. Vacuum hoses incorporated in many designs to suction cerumen out of receiver tubing have probably damaged as many units as they have helped, and have not addressed cerumen buildup within the receivers themselves.

Typical cerumen is composed of solid, liquid, and gaseous elements. It has acids, fats, cholesterol, lipids, oils, inert matter, and heavy metals. Each cerumen component has its own vapor pressure, specific gravity, particle mass, molecular structure, and bonding characteristic. Cerumen is also acidic, ranging from 4.0 to 6.1 on the pH scale.

Complicating the issue is that there are two general categories of cerumen. Dry cerumen has dense, waxy characteristics. It is very visible upon otoscopic examination of the ear. It is this type of cerumen that impacts the ear canal itself, often requiring medical intervention to remove the blockage. In ear-worn devices, this type of cerumen typically clogs up the receiver tube, and is relatively easy to remove. Liquid cerumen has oily, fatty characteristics, and is often undetected during otoscopic examination. It is this type of cerumen that most readily invades ear-worn instrument components.

The typical ear level communication device has electronic components including a receiver, which is analogous to a speaker. This receiver becomes saturated with cerumen over time as a result of the capillary action of liquid cerumen. The receiver itself is electrically charged, drawing atomized cerumen into all areas of the receiver by the charged, sound generating diaphragm. The receiver further acts as a heat sink. During the heating cycle caused by the warm ear and the heat generated due to electrical operation, it is likely that a creep factor causes the wax to flow to the receiver. The cooling cycle, which occurs during the turned offmode when the device is sitting at rest, facilitates congealing of the liquid cerumen within the receiver. The resulting added mass of the cerumen on the receiver diaphragm causes low output distortion and loss of high frequency response. In addition, acids within the cerumen cause deterioration of the diaphragm suspension, resulting in receiver failure.

Applying the principles of angular acceleration to a complex body excretion such as cerumen addresses a multitude of chemical elements in various states. Subjecting centripetal acceleration to this chemical composite causes cerumen to separate into high mass particles and low mass particles. Those low mass particles have a lower vapor pressure, and are subject to centrifugal evaporation. The normal force of acceleration concurrently drives the high mass particles out of the device as a function of gravitational force.

The following U.S. patent documents are incorporated herein by reference: 2003/0196687; 2003/0198361; 2002/0126864; 5,404,105; 4,901,391; 5,898,972; 2,675,814; 4,953,215.

U.S. Publication No. 2003/0196687 discusses generally cleaning cerumen or earwax out of a hearing aid, by using a centrifuge, see paragraph (0051).

U.S. Pat. Nos. 5,898,972 and 4,901,391 disclose tools used to clean earwax from a hearing aid.

U.S. Patent/Publication Nos. 5,404,105 and 2002/0126864 disclose kits or multi-use devices for cleaning and maintaining a hearing aid.

BRIEF SUMMARY OF THE INVENTION

The present invention provides an improved method and apparatus for cleaning a hearing aid of cerumen. The method and apparatus each employ a rotating chamber having opposed openings fitted with specially configured retainers that gently support a hearing aid, even when it is rotated at speeds of, for example between about 1000 and 12,000 revolutions per minute or rpms (preferably between about 2800 and 3200 revolutions per minute).

The present invention provides a method of cleaning a hearing aid that includes the steps of providing a rotary chamber, supporting the hearing aid in the chamber, supporting a counterweight upon the chamber, and separating cerumen from the hearing aid by rotating the chamber at a high rate of speed of between about 2800 and 3200 revolutions per minute and for a time period, e.g. about less than a minute, preferably between about 18 and 22 seconds.

The method can include providing a receptacle fitted to the chamber and wherein the hearing aid is supported in part by the chamber.

In one embodiment, the method can include providing a flexible frame fitted to each of the openings wherein a hearing aid is supported by one of the flexible frames and a counterweight or another hearing aid is supported in the other of the flexible frames.

There can be two openings that are spaced about 180 degrees apart. There can be three openings that are spaced about 120 degrees apart. There can be four or more openings that are spaced equally apart, such as for example four openings spaced 90 degrees apart.

The chamber spins to extract cerumen, the cerumen collecting in a container or on the rotary chamber receptacle.

In a second embodiment of the apparatus of the present invention, the position of the counterweight can be adjusted relative to the position of the hearing aid.

The present invention provides an improved hearing aid cleaner apparatus that includes a housing having an interior and a motor drive contained within the housing interior. A motor drive is mounted to the housing and the drive shaft couples the motor drive and the chamber. The rotary chamber has one or more receptacles mounted to the chamber, each receptacle being configured to hold a hearing aid or a counterweight. The motor drive is powered sufficiently to rotate the hearing aid at a speed of between about 2800 and 3200 rpm and for a time period of between about 18 and 22 seconds.

The present invention incorporates a centripetal accelerator which creates a force of between about 200-400 G's (200-400 times the force of gravity on earth at sea level) on the device to be cleaned. Cerumen is sheared into separate particles of varying mass, density, specific gravity, vapor pressure, molecular structure, and bonding characteristics.

The shearing action of the angular force enables low vapor pressure contaminants and volatile toxins to evaporate. The remaining lipids, cholesterol, and other high mass components of cerumen are ejected by their own inertia.

In a preferred embodiment, this action is enhanced by introducing a cleaning solution. Such a solution might be a Part A only solution or a Part A and Part B solution.

The typical solution might include combinations of mineral oil, isopropyl alcohol, and hydrogen peroxide. The present invention incorporates a cleaning solution that is equal parts isopropyl alcohol and hydrogen peroxide housed in a squeeze bottle with blunted needle applicator through which the solution can be inserted into the receiver tube until the tube is filled. The solution is then agitated by a wax probe inserted into the receiver tube and rotated in a circular motion. Following that, the instrument is placed back into the apparatus of the invention, and the cleaning cycle is repeated.

In yet another embodiment, ultrasonic vibration is introduced on the longitudinal axis, perpendicular to the rotation, of the device to be cleaned. This action further enhances the particle separation.

In still another embodiment, heat is added to the cleaning chamber, about 105-140° F. (about 41-60° C.), to make the ear wax more liquid and soft.

A prototype unit was constructed with a small 12 V DC variable speed (0-12,000 rpm) motor, 12 V DC power supply, momentary contact switch for activation, rheostat for speed control, plastic cup for device placement, aluminum housing for a base, and polycarbonate cover for safety and wax collection.

Initial testing of actual devices determined that a time of 20 seconds at a speed of approximately 3000 rpm was sufficient to expel contaminants from the aperture of the device.

Further testing showed that different devices have negative effect on the rotational characteristics of the machine. Effects included vibration and inconsistent speed. Table 1 will show the effect of different simulated device weights on ultimate speed. The same simulated devices were also tested with an equal and opposite counter balance as shown in Table 2.

TABLE 1

| No Counterbalance | | | |
| --- | --- | --- | --- |
| Weight (g) | Low (rpm) | Medium (rpm) | High (rpm) |
| 0 | 3900 | 5000 | 6593 |
| 1 | 3306 | 4084 | 5579 |
| 2 | 2866 | 3434 | 4750 |
| 3 | 2696 | 3325 | 4610 |
| 4 | 2464 | 3053 | 4259 |
| 5 | 2283 | 2887 | 3900 |
| 6 | 2170 | 2670 | 3740 |

TABLE 2

| Counter Balance | | | |
| --- | --- | --- | --- |
| Weight (g) | Low (rpm) | Medium (rpm) | High (rpm) |
| 0 | 3900 | 5000 | 6593 |
| 1 | 3700 | 4700 | 6400 |
| 2 | 3820 | 4760 | 6230 |
| 3 | 3990 | 4979 | 6695 |
| 4 | 4179 | 5195 | 6530 |
| 5 | 3660 | 4628 | 6191 |
| 6 | 3193 | 3926 | 5071 |

A possible electronics design consists of a timing circuit to run the 12V motor. The motor can be activated by a normally-open momentary push button switch. Preferably, once depressed, the motor will run for approximately 20 seconds and then shut off automatically.

A microcontroller can be used to control both the run duration as well as speed of the device. For safety concerns, braking of the system can be electronic or mechanical. Braking can include the use of a counter-balance in the device holder.

This can be accomplished by using similar device weights or by molding a counter-balance into the cup. The cup may also be capable of handling multiple devices, thereby negating the need for a counter-balance.

A possible electronics design consists of a timing circuit to run the 12V motor.

The motor can be activated by a normally-open momentary push button switch.

Preferably, once depressed, the motor will run for approximately 20 seconds and then shut off automatically.

A microcontroller can be used to control both the run duration as well as speed of the device. For safety concerns, braking of the system can be electronic or mechanical. Braking can include the use of a counter-balance in the device holder.

This can be accomplished by using similar device weights or by molding a counter-balance into the cup. The cup may also be capable of handling multiple devices, thereby negating the need for a counter-balance.

An advantage of the present invention over prior methods of cleaning hearing aids is that hearing aids can be cleaned using centrifugal force without the necessity of heat being applied. That is, the hearing aid can be properly cleaned even if no heat is applied to the hearing aid as it is being rotated, or prior to it being rotated, in the centrifuge.

As used herein, hearing aid refers to custom and non-custom hearing aids to amplify sounds and like electronic hearing devices, such as hearing protectors and tinnatus maskers having the shape of typical hearing aids to amplify sounds. That is, the apparatus of the present invention can be used to clean all such devices.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
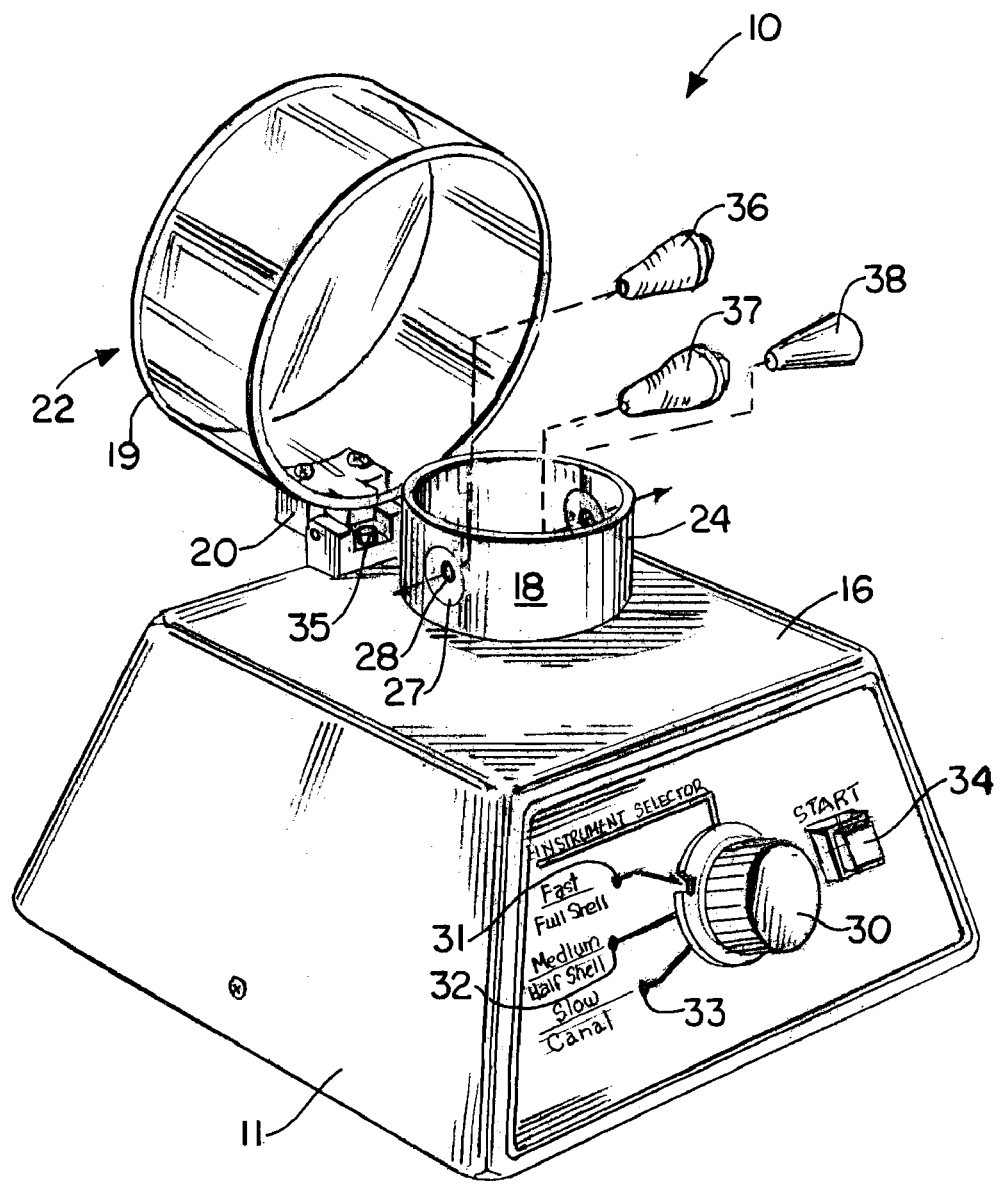
FIG. 1 is a perspective view of the preferred embodiment of the apparatus of the present invention.
Figure 2:
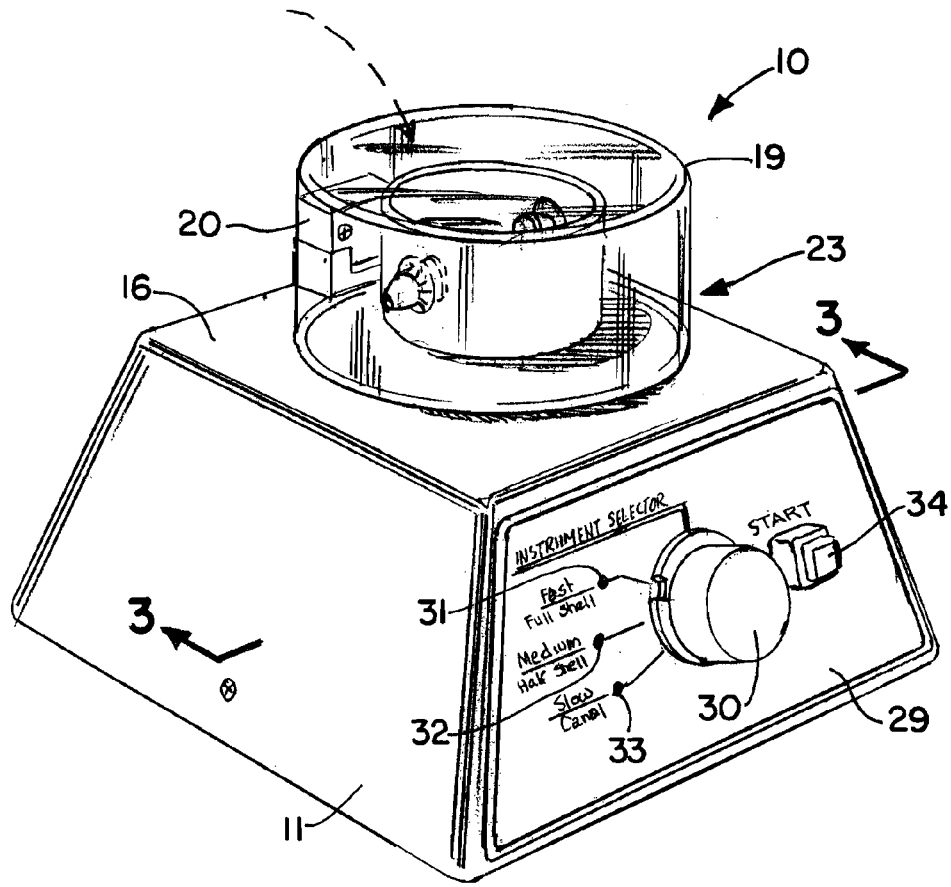
FIG. 2 is a perspective view of the preferred embodiment of the apparatus of the present invention showing the closed, operating position.

FIGS. 1-5 show the preferred embodiment of the apparatus of the present invention designated generally by the numeral 10. Hearing aid cleaner apparatus 10 provides a housing 11 with an interior 13 for containing motor drive 12 and speed control 29. The motor drive 12 can be controlled with a speed control 29 having a control knob 30 that extends externally of housing 11 as shown in FIGS. 1 and 2.

Motor drive 12 can be powered with a power supply 14 of for example 12 volts.

Housing 11 has multiple sidewalls 15 and can include an upper wall 16. Housing 11 can be supported by a plurality of feet 21. A drive shaft 17 extends from motor drive 12 upwardly through upper wall 16 to form a connection with rotary chamber 18. In this fashion, when motor drive 12 is activated using knob 30 and speed control 29, rotary chamber 18 spins at a selected revolutions per minute.

Cover 19 can be a generally cylindrically shaped structure that is mounted to housing 11 using hinge 20. Hinge 20 can be provided with cover switch 35 that deactivates motor drive 12 when the cover 19 is in the open position of FIG. 1.

When the cover 19 is moved to the closed position of FIG. 2, cover switch 35 is depressed and motor drive 12 can be operated using speed control 20. In FIGS. 1 and 2, the open position is designated generally by the numeral 22 while the closed position is designated generally by the numeral 23 in FIG. 2. Preferably, there is a fuse 107 electrically connected between the power supply 14 and cover switch 35.

Figure 1B:
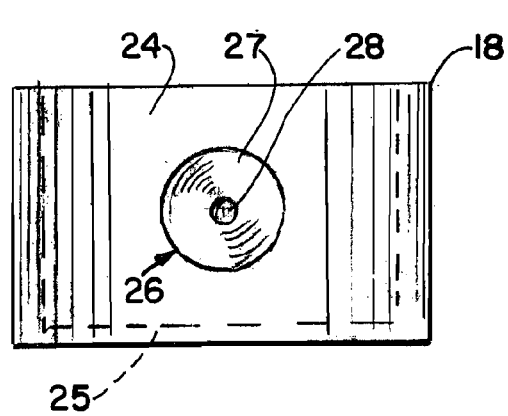
FIG. 1B is another fragmentary view of the preferred embodiment of the apparatus of the present invention.
Figure 1A:
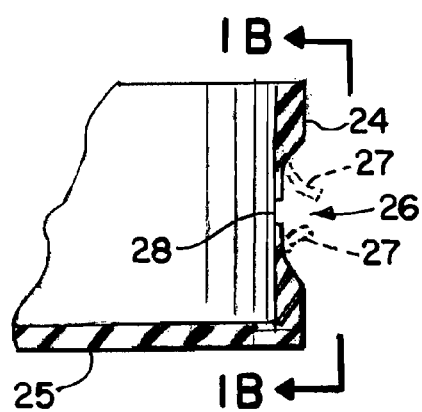
FIG. 1A is a fragmentary view of the preferred embodiment of the apparatus of the present invention.
Figure 3:
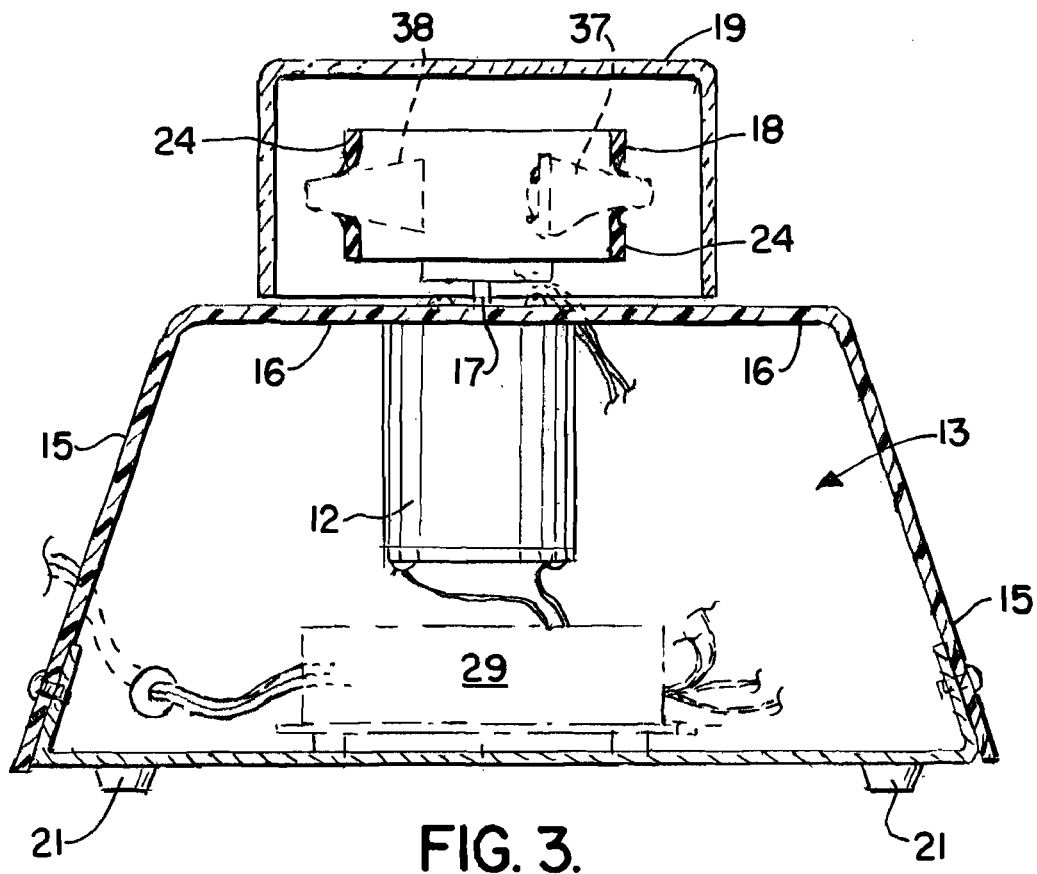
FIG. 3 is a sectional elevation view taken along lines 3-3 of FIG. 2.
Figure 4:
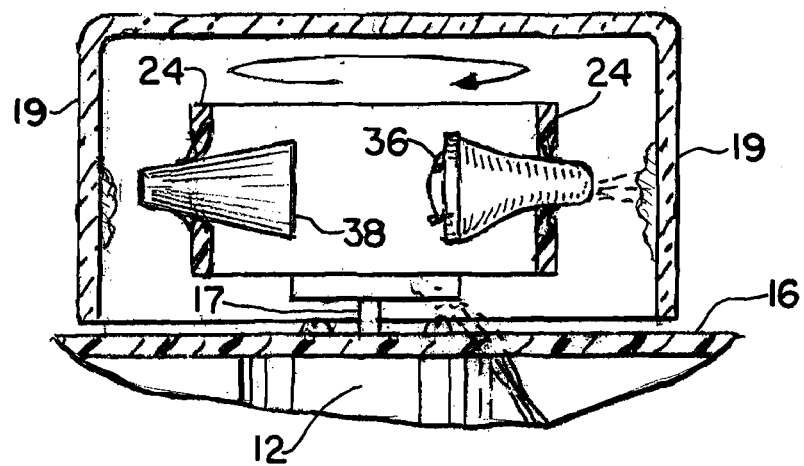
FIG. 4 is a fragmentary, sectional view of the preferred embodiment of the apparatus of the present invention.

Rotary chamber 18 provides a cylindrically shaped sidewall 24 that can be of a plastic, rubber, or like material. Rotary chamber 18 also includes a circular bottom wall 25 to which cylindrical sidewall 24 is attached, preferably a unitary structure. One or more openings 26 are provided in sidewall 24. Each opening 26 is fitted with an annular flexible section 27 having an opened center 28. The annular flexible section 27 (see FIG. 1B) can be of rubber or plastic, but preferably thinner than the cylindrical sidewall 24 as shown in FIG. 1A. The sidewall 24 thus has a thickness of between about 0.10 and 0.15 inches (0.254 and 0.381 cm). The flexible annular section 27 preferably has a thickness of between about 0.040 and 0.060 inches (0.1016 and 0.1524 cm).

The control knob 30 can be placed in a number of different positions, each designating a different rotational speed for rotary chamber 18. As an example, the knob 30 can be set to fast position 31, medium position 32 or slow position 33. As an example, the rotary chamber 18 will rotate at a speed of between about 4200 and 4400 revolutions per minute (r.p.m.) when the knob 30 is set to the fast position 31. The rotary chamber 18 will rotate at a speed of between about 3500 and 3700 revolutions per minute (r.p.m.) when the knob 30 is set at the medium position 32. The rotary chamber 18 will rotate at a speed of between about 3000 and 3200 revolutions per minute (r.p.m.) when the knob 30 is set at the slow position 33. Indicator light 34 indicates to an operator when the rotary chamber 18 is in the operating, spinning position, having been activated by motor drive 12 and knob 30.

One or more hearing aids 36, 37 can be placed in the spaced apart openings 26.

Alternatively, a hearing aid 36 or 37 and a counterweight 38 can be placed in the two spaced apart openings 26 shown in the drawings. While two openings 26 are shown in the drawings, it should be understood that one opening 26 can be provided and rotary chamber 18 counterweighted. Thus, the counterweighted chamber 18 will rotate smoothly even when fitted with a single opening 26 and a single hearing aid 36 or 37 to be cleaned. Two, three or more openings 26 can be provided, each fitted with annular flexible section 27 for supporting a hearing aid 36, 37 or a counterweight 38.

Figure 5:
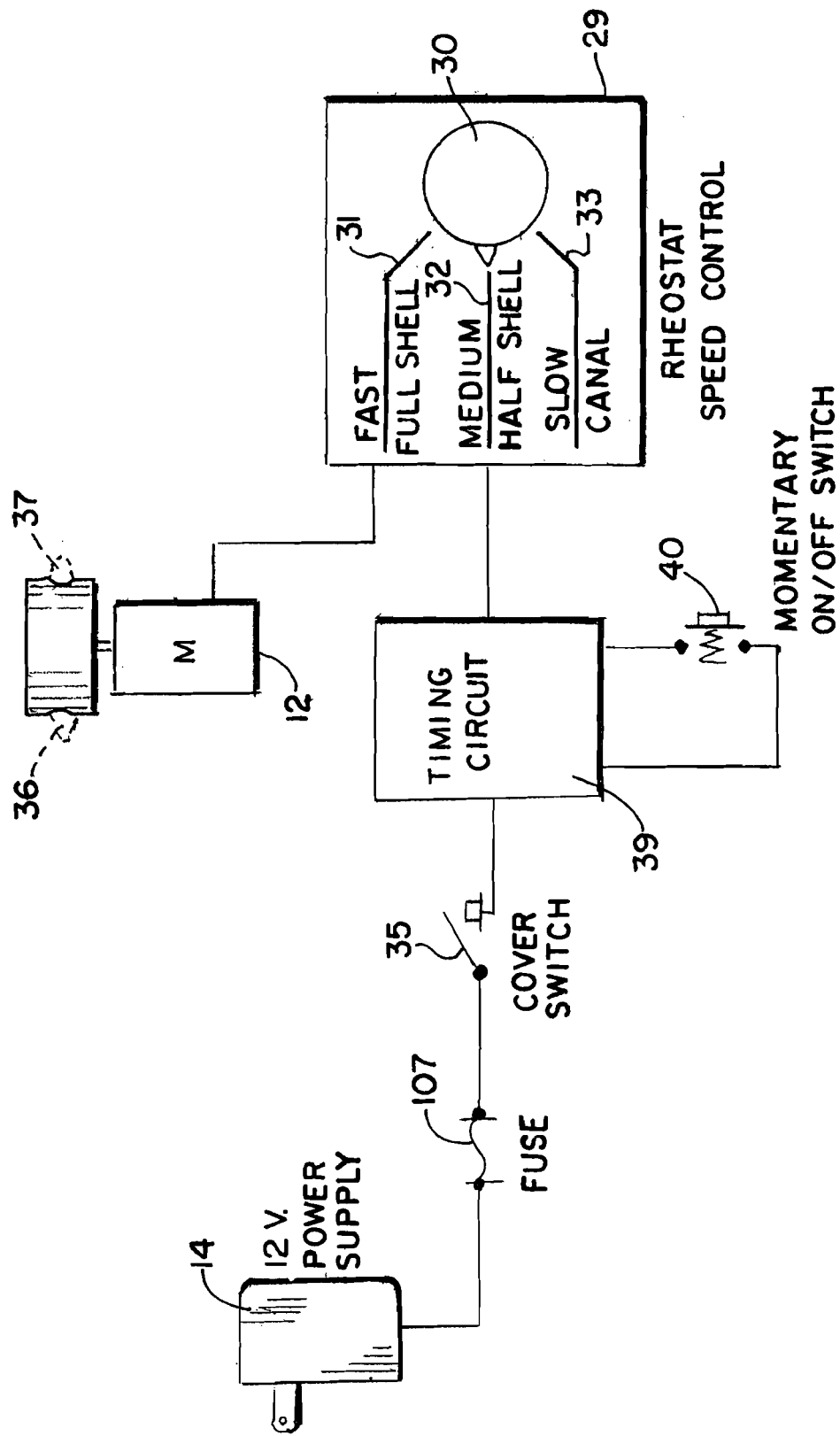
FIG. 5 is a schematic view of the preferred embodiment of the apparatus of the present invention.
Figure 6:
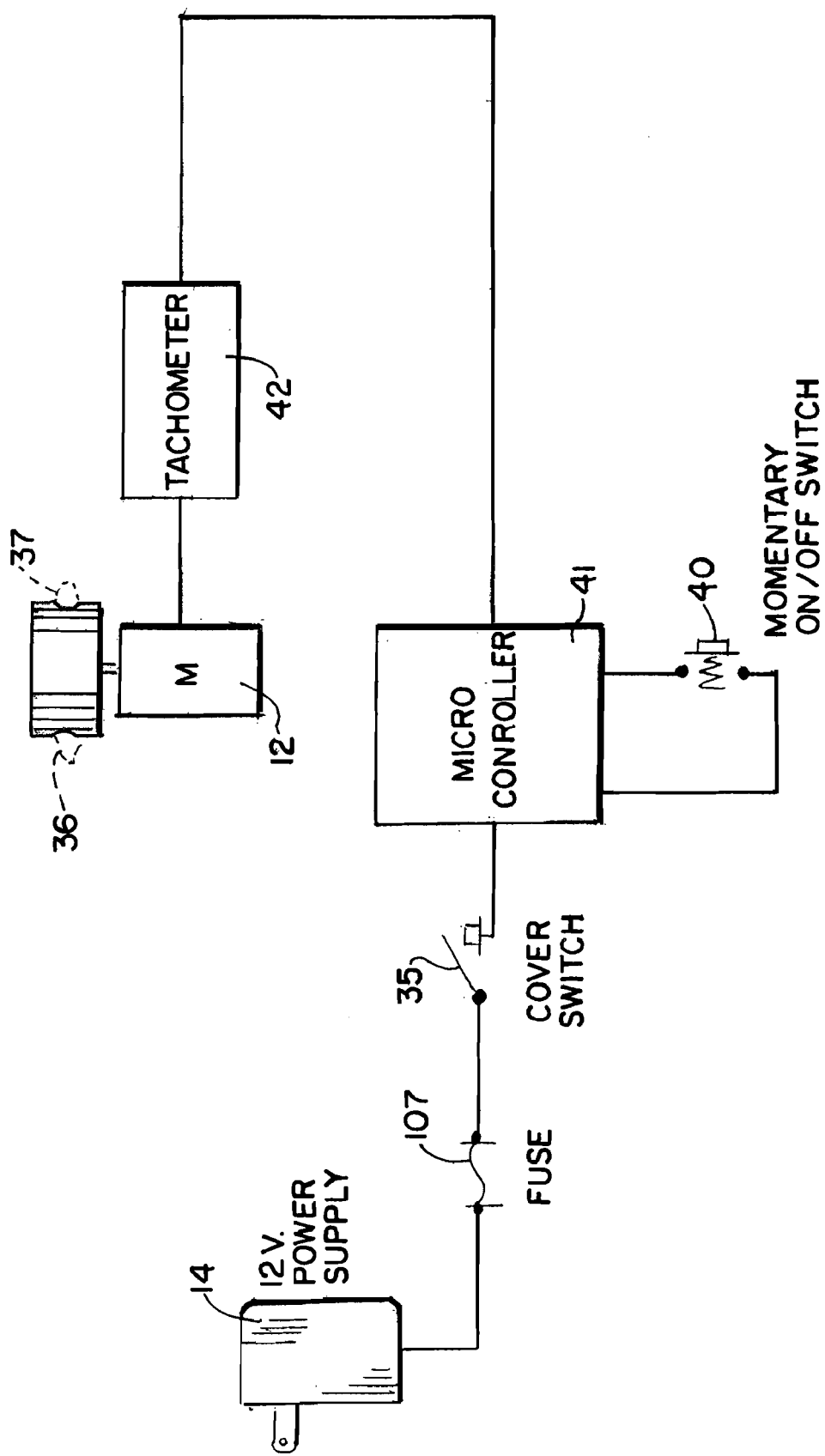
FIG. 6 is a schematic view of an alternate embodiment of the apparatus of the present invention.

In FIG. 5, a timer circuit 39 and a momentary on/off switch 40 can be provided as shown. In the embodiment of FIG. 6, the timing circuit 39 and speed control 29 are replaced with a microcontroller 41 and tachometer 42. The speed control for the centrifuge is designed to have a speed of approximately 3000 rpm for each speed selection (Slow, Medium and Fast). The reason for this is that as the mass of the hearing device increases, the motor speed decreases. To compensate for the increase in mass, a higher speed will be selected in order to maintain the 3000 rpm.

This is an approximate speed as the circuitry was designed by averaging representative samples of all the different styles and sizes of hearing instruments. The associated speeds for the centrifuge with no hearing device inserted are as follows:
  Slow:≈3000-3200
  Medium:≈3500-3700
  Fast:≈4200-4400

Figure 7:
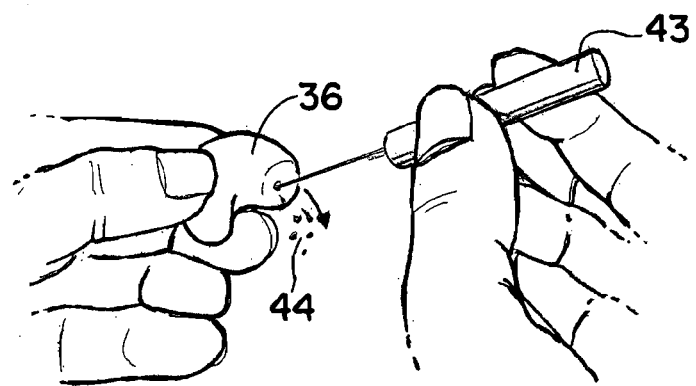
FIGS. 7, 8 and 9 are perspective views illustrating certain steps of the method of the present invention.
Figure 8:
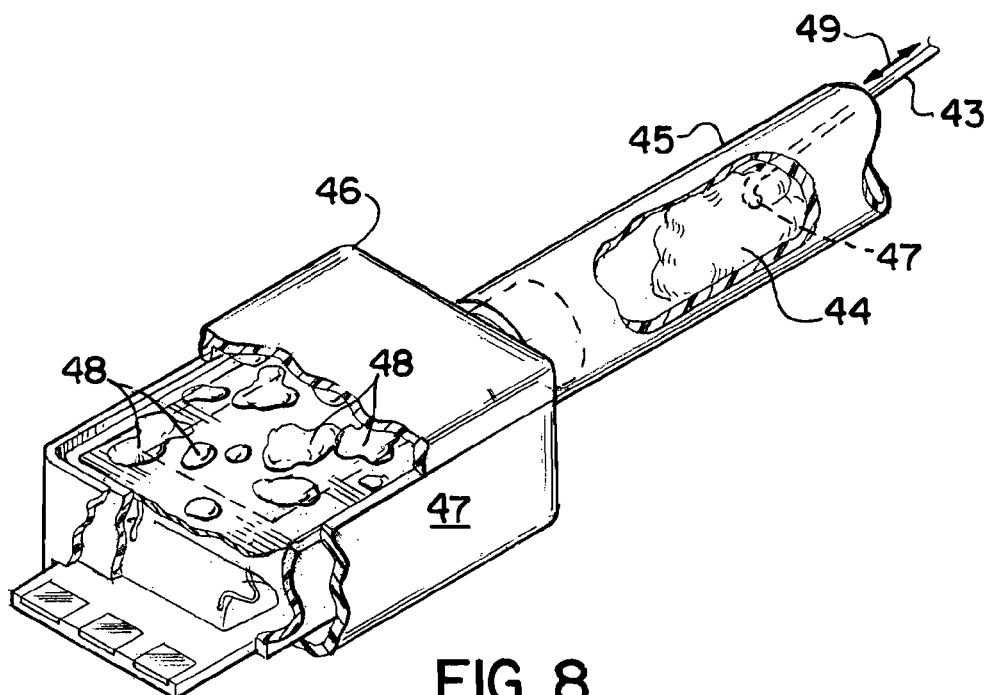
Figure 9:
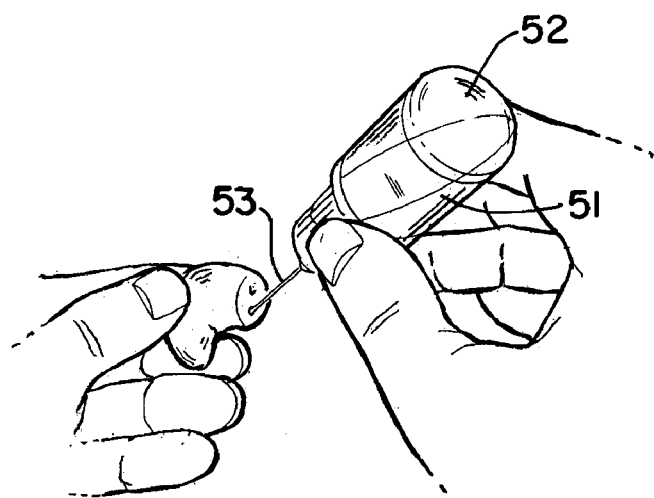

FIGS. 7-9 show preliminary preparation of a hearing aid 36 before placement in cleaner apparatus 10. A probe 43 is used to clean hard wax 44 from hearing aid 36. Such hard wax 44 usually resides in receiver tube 44. A back and forth movement of probe 43 (see arrow 49 in FIG. 8) dislodges such hard wax 44. A liquid solvent 51 can be added to assist in removal of hard wax 44. Such solvent can be a mixture (e.g. 50% each) of alcohol and hydrogen peroxide, which is an antimicrobial agent. The alcohol can be isopropyl alcohol. The mixture can also optionally include mineral oil. Solvent 51 can be contained in bottle 52 having blunt needle 53.

Figure 10:
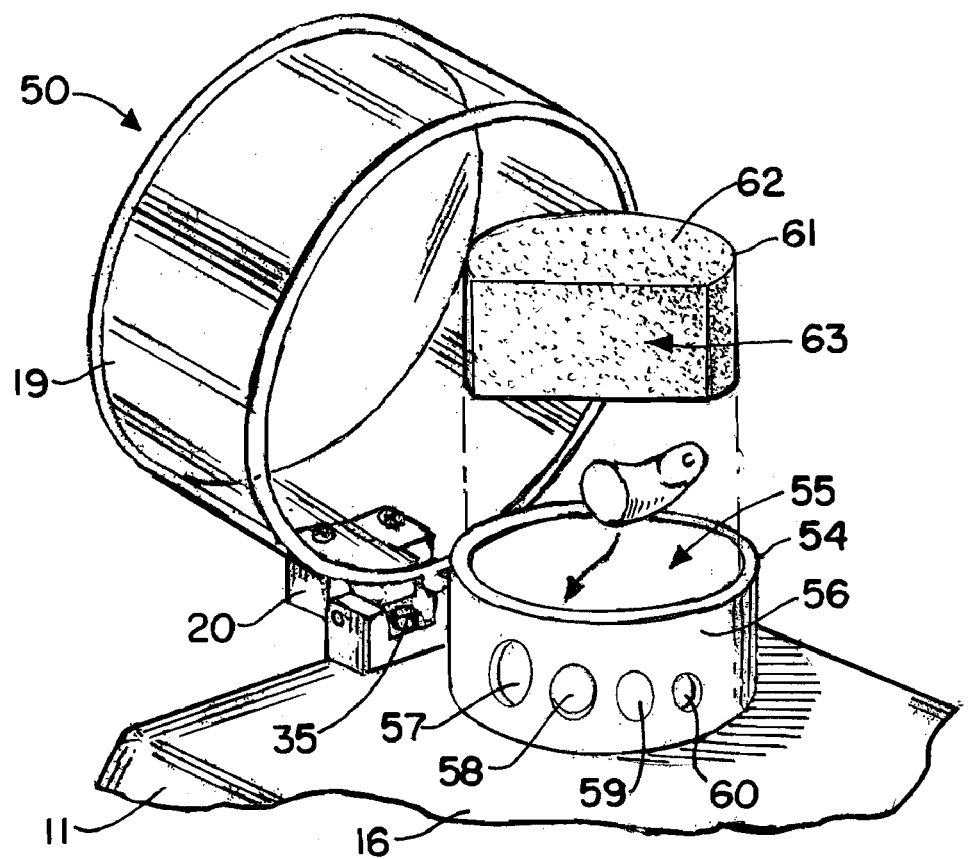
FIG. 10 is a perspective view of a second embodiment of the apparatus of the present invention.
Figure 11:
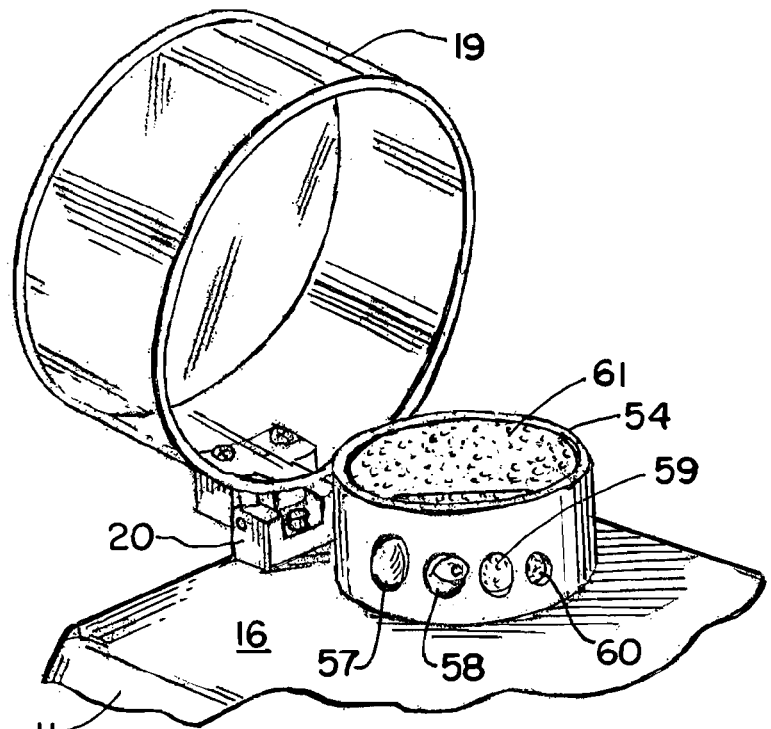
FIG. 11 is a perspective view of the second embodiment of the apparatus of the present invention.
Figure 12:
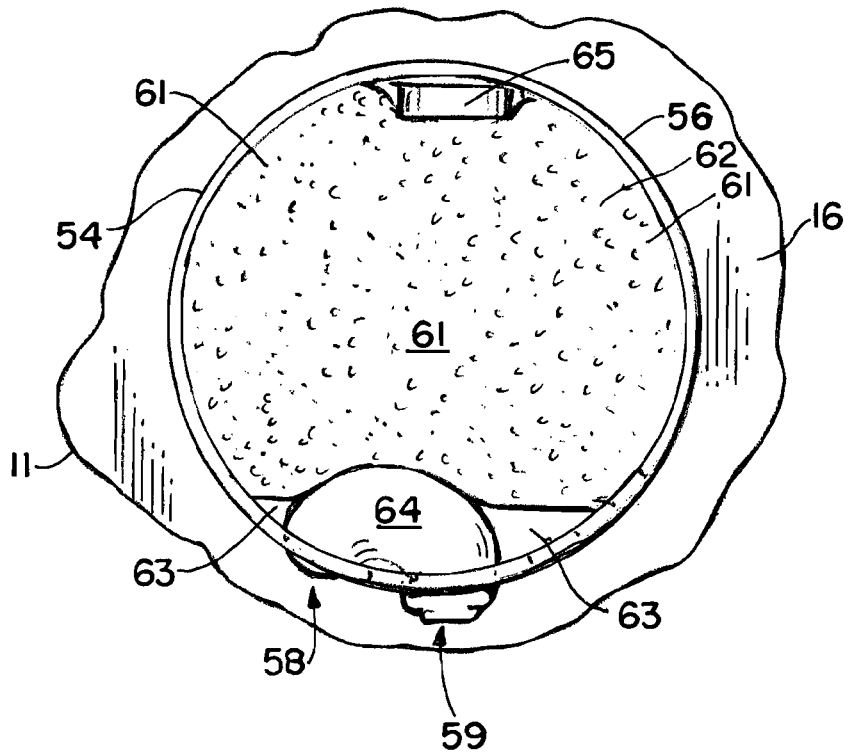
FIG. 12 is a perspective view of the second embodiment of the apparatus of the present invention.

In FIGS. 10-12, a second embodiment of the apparatus of the present invention is shown, designated generally by the numeral 50. Hearing aid cleaner apparatus 50 can use many components common to the preferred embodiment that is shown in FIGS. 1-6 and designated by the numeral 10. In that regard, hearing aid cleaner apparatus 50 provides housing 11 having an interior 13 that contains a motor drive 12 for driving a drive shaft 17 that rotates rotary chamber 54. Cover 19 can be connected to housing 11 with hinge 20. The hinge 20 can provide a switch 35 that disallows operation of the apparatus 50 until the cover 19 is rotated upon hinge 20 to a lower, closed position as shown for the preferred embodiment in FIG. 2. Hearing aid cleaner apparatus 50 can provide a speed control 29 having a knob 30 that can be placed in multiple rotational speed positions including a slow position 33, a medium speed position 32, and a fast speed position 31 as with the preferred embodiment.

Hearing aid cleaner apparatus 50 provides a rotary chamber 54 having an interior 55. The interior 55 is surrounded by cylindrical wall 56 portion of rotary chamber 54. As with the preferred embodiment, the rotary chamber 54 can have a circular bottom wall such as the circular bottom wall 25 provided with rotary chamber 18 of the first embodiment.

Cylindrical wall 56 is provided with a plurality of openings 57, 58, 59, 60. A foam body 61 can be placed inside rotary chamber 54, occupying a majority of interior 55 as shown. The foam body 61 can be generally cylindrically shaped, having a cylindrical section 62, but providing a cut-out 63 that is occupied by hearing aid 64 during spinning and removal of earwax from hearing aid 64. A counterweight 65 can optionally be positioned opposite hearing aid 64 as shown in FIG. 12. The hearing aid 64 shown in FIG. 5 can be generally u-shaped, protruding through one or more openings 57, 58, 59, 60 of rotary chamber 64 as shown.

Figure 13:
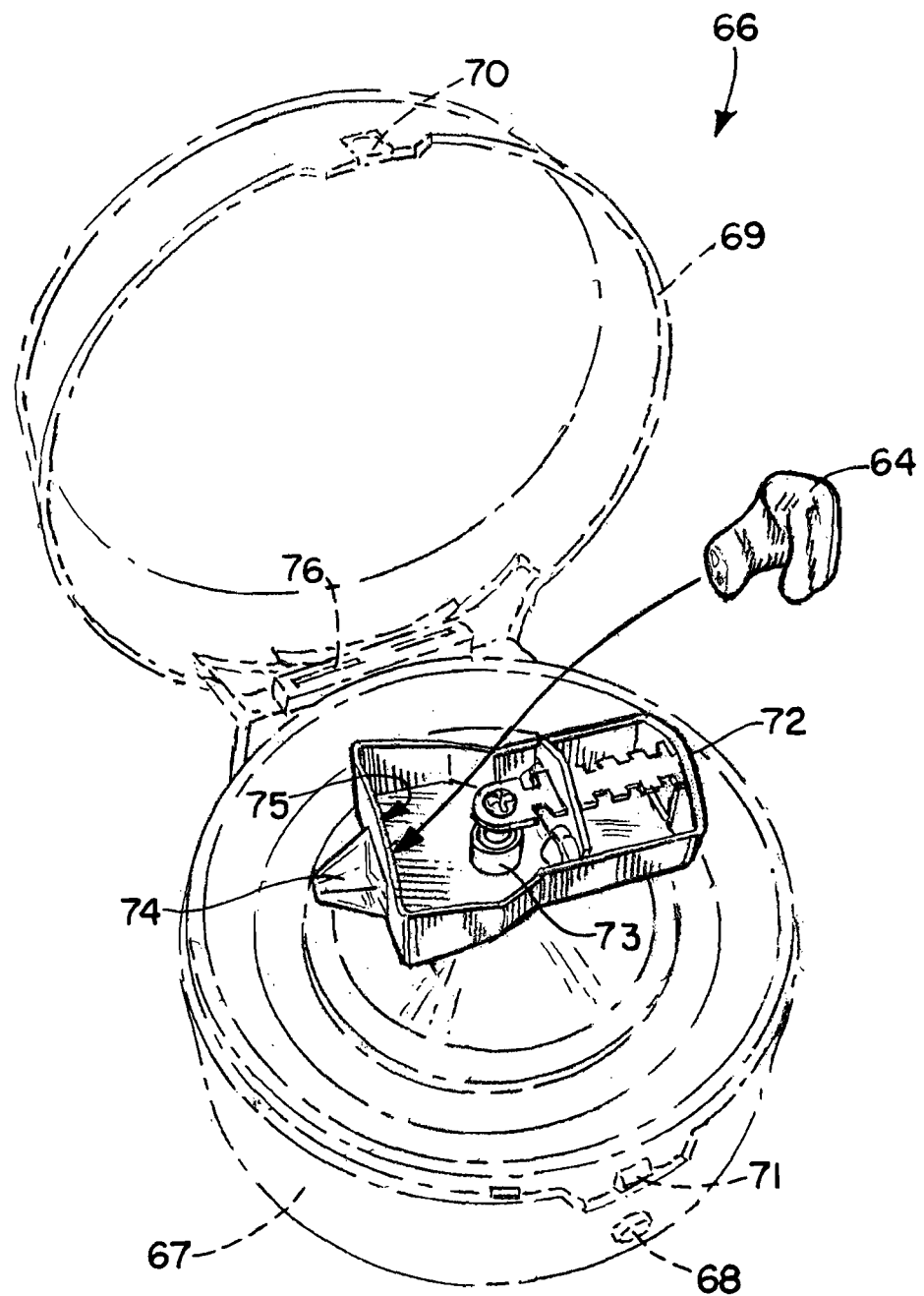
FIG. 13 is a perspective view of an alternate embodiment of the apparatus of the present invention.
Figure 14:
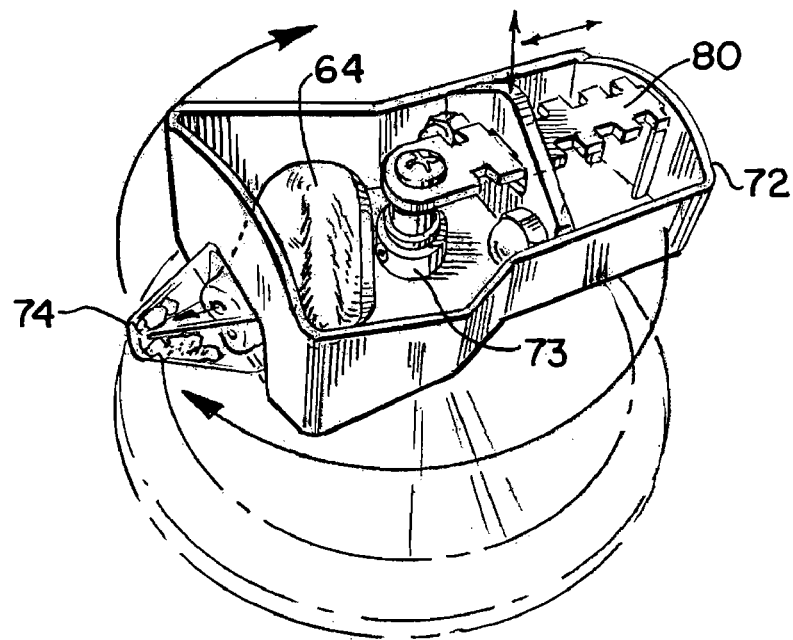
FIG. 14 is a fragmentary perspective view of the alternate embodiment of the apparatus of the present invention.
Figure 15:
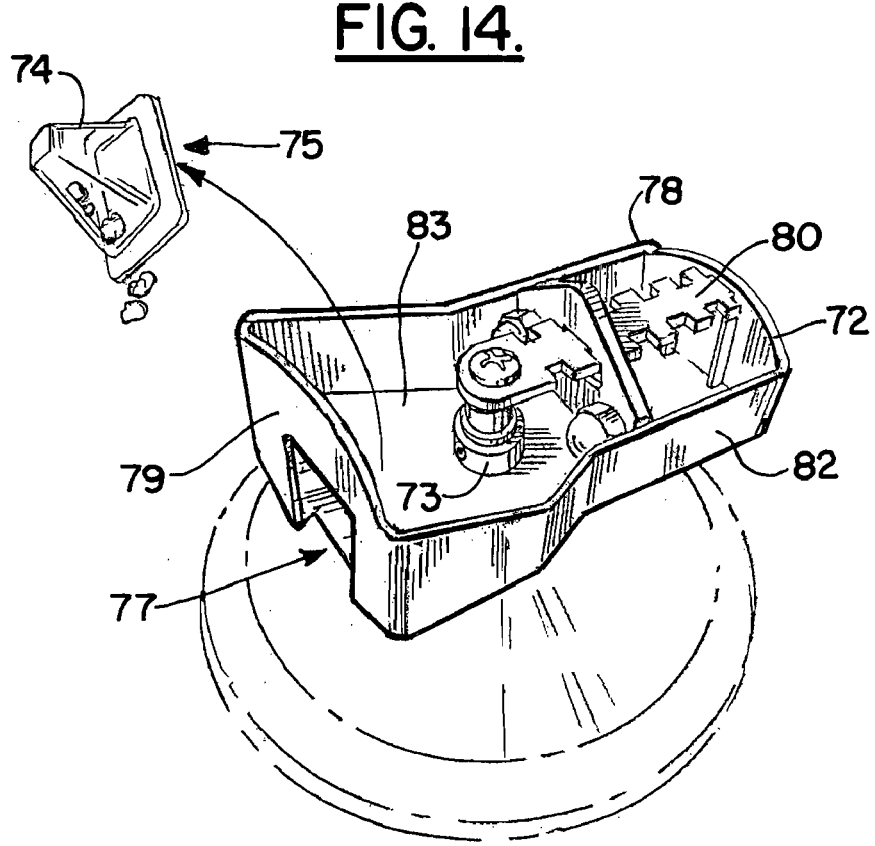
FIG. 15 is another fragmentary perspective view of the alternate embodiment of the apparatus of the present invention.

FIGS. 13-20 show an alternate embodiment of the apparatus of the present invention and illustrate the method of the present invention. Hearing aid cleaner apparatus 66 in FIGS. 13-15 provide a base/motor drive to which can be connected a rotary chamber 72. The base/motor drive has a switch 68 that can be used to activate the motor drive. The motor drive is preferably provided with a timer that operates the motor drive at a selected revolution per minute and for a selected period of time, such as for example between about 5 and 60 seconds or about 18-22 seconds. A cover 69 can be provided with spaced apart latch parts 70, 71. The latch parts 70, 71 or hinge 76 can be provided with a switch that disengages the motor drive from rotating the rotary chamber 72 unless the cover 69 is in a closed position. Cover 69 pivotally attaches to base/motor drive 67 with hinge 76.

The rotary chamber 72 is mounted on hub 73 to a drive shaft (not shown) such as the drive shaft 17 that is provided with motor 12 and housing 11 of the preferred embodiment of FIGS. 1-12.

Rotary chamber 72 has hub 73 mounted to bottom wall 83. Rotary chamber 72 provides bottom wall 83 and sidewall 82. Rotary chamber 72 has opposed end portions including a counterweight end portion 78 and a receptacle end portion 79.

The receptacle end portion 79 provides an opening 77 that is receptive of receptacle 74. Receptacle 74 can be cone shaped as shown in FIG. 15, providing a concavity 75 for collecting material such as ear wax that is removed from hearing aid 64.

A radially extending support 80 extends between hub 73 and sidewall 82 as shown in FIGS. 14, 15 and 19-20. Fastener 81 can be used to secure support 80 to hub 73.

A counterweight 90 can be moved into various positions along support 80. The counterweight 90 can be selectively moved by the thumb and forefinger of a user 97 in order to determine the best location for the counterweight 90 to minimize vibration during spinning of rotary chamber 72. The counterweight 90 provides a plate 94 to which is attached a pair of spaced apart weights 95, 96. The counterweight 90 provides a t-shaped opening 91 that includes a lower slot 92 that is generally rectangular and an upper slot 93 that is generally rectangular. The lower slot 92 is much larger than the upper slot 93.

Figures 19, 20:
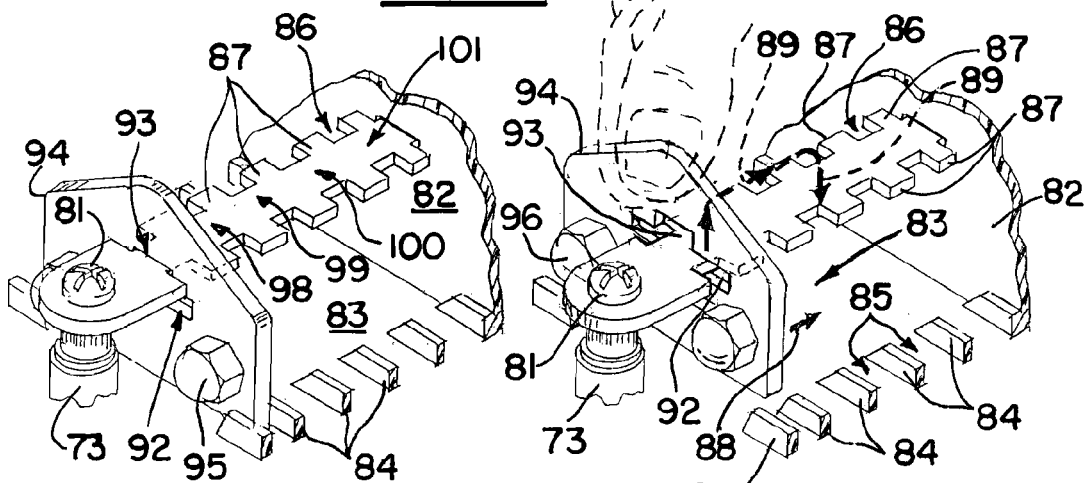
FIG. 19 is a partial perspective view of the alternate embodiment of the apparatus of the present invention.
FIG. 20 is a partial perspective view of the alternate embodiment of the apparatus of the present invention.

A plurality of stops are provided for indexing the plate 94 into multiple positions such as the five positions shown in FIGS. 19 and 20, each position being indicated generally as a slot 86 on support 80 and as a space 85 in between stops 84 that are mounted to bottom wall 83 of rotary chamber 72.

The slots 85 are receptive of a lower end portion of plate 94. The slots 86 are receptive of plate 94 on opposing sides of upper slot 92 of t-shaped opening 91. Stops 87 of support 80 define its widest part. The support 80 at stops 87 provides a cross sectional area that is about the same size and shape as the cross sectional area of upper slot 93. Thus, when the plate 94 is elevated so that lower slot 93 is at the same elevation as support 80 (see FIG. 20) the user 97 can slide the plate 94 to align it with any pair of slots 86 and thus any one of the selected positions along support 80. When a selected position is reached, the user 97 simply lowers the plate 94 so that the upper slot 93 is next to a pair of slots 86 and the plate 94 can be lowered so that the upper slot 93 now is aligned with the support 80, that position being shown in FIG. 19. In FIG. 19, the plate 94 has been placed closest to hub 73. In FIG. 19, there are four additional positions that are designated generally as positions 98, 99, 100, 101.

The weights 95, 96 can be varied in weight. In FIG. 20, arrow 89 indicates the path of plate 94 when it is moved from one position to another position such as position 100. Arrow 88 in FIG. 20 illustrates schematically the travel of plate 94 from a position next to hub 73 to a position spaced away from hub 73.

Figure 16:
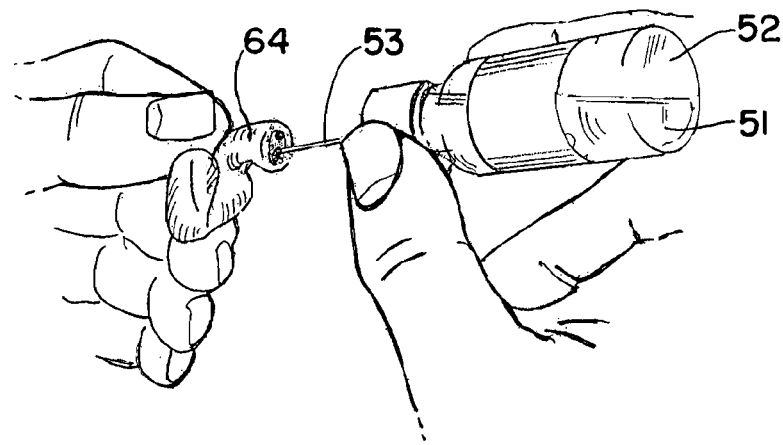
FIG. 16 is a perspective view illustrating a method step of the present invention, the contacting of material to be removed from the hearing aid with a solvent material.
Figure 17:
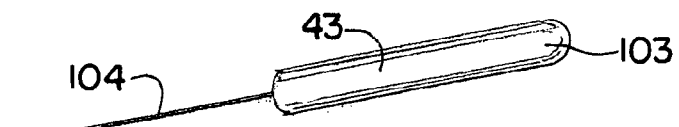
FIG. 17 is a perspective view illustrating a tool that can be used as part of the method of the present invention.

FIGS. 16 illustrates that as part of the method of the present invention, it is preferred that hearing aid 64 containing ear wax to be removed be preliminarily treated with a solvent 51 contained in bottle 52. Bottle 52 can be provided with a needle 53 as with the preferred embodiment. The solution can be a combination of water, alcohol, and hydrogen peroxide such as was described with respect to the preferred embodiment of FIGS. 1-12.

Figure 18:
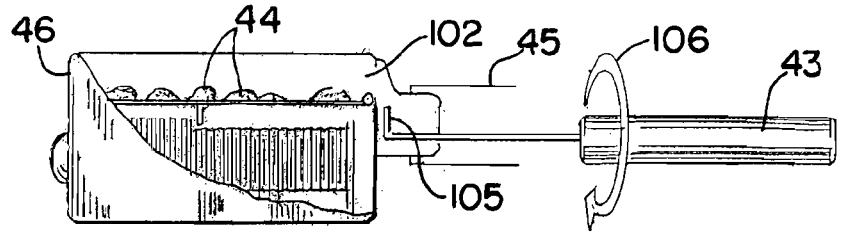
FIG. 18 is a schematic view illustrating removal of material from a part of the hearing aid.

A tool 43 (see FIG. 17) is preferably used to remove ear wax that might be clogging opening 102 of receiver 46. Receiver 46 is shown in FIG. 18 as connected to tube 45 (see FIG. 8). Tool 43 provides a handle 103 and probe 104 having L-shaped end portion 105. The L-shaped end portion 105 is rotated by rotating handle 103 as indicated schematically by arrow 106 in FIG. 18. This rotating action of L-shaped end portion 105 of probe 104 clears any hard wax 44 that has accumulated near opening 102 and clears the way for centrifuge removal of hard wax 44 and soft wax from receiver 46 via opening 102 and tube 45. As with the preferred embodiment, the tube 45 is oriented generally horizontally in rotary chamber 72 when base/motor drive 67 rotates rotary chamber 72. This orientation in a generally horizontal position of tube 45 and receiver 46 can be achieved by using a generally vertical wall 82 at opening 77.

The distance between the cover and the rotor is sufficient to allow a typical hearing aid or hearing protector to rest on the rotor with enough clearance to allow the cover to close and the rotor to freely rotate.

The method of cleaning a hearing aid involves separating cerumen from the hearing aid by rotating the chamber at a high rate of rotation speed of at least about 2000 rpms. While 200-400 G's is preferred, in general one wishes to apply as much force as possible without harming the instrument. Increasing the force can be achieved by rotating the device faster or increasing the distance of the hearing aid from the center, or a combination of the two. When the center of a hearing protector or hearing aid is at a distance of about 37.5 mm from the center, 2200 rpm is probably the minimum speed at which useful results will be achieved in about 20 seconds. At this distance, a well made new hearing protector or hearing aid can withstand a rotational speed of up to about 12000 rpm for about 20 seconds.

Typically, in a practically sized centrifuge of the present invention, a hearing aid will be positioned such that its center of gravity is about 25 mm-50 mm (preferably 30-40 mm) from the center of rotation of the centrifuge.

The following is a list of parts and materials suitable for use in the present invention.

| PARTS LIST | |
| --- | --- |
| Part Number | Description |
| 10 | hearing aid cleaner apparatus |
| 11 | housing |
| 12 | motor drive |
| 13 | interior |
| 14 | power supply |
| 15 | sidewall |
| 16 | upper wall |
| 17 | drive shaft |
| 18 | rotary chamber |
| 19 | cover |
| 20 | hinge |
| 21 | foot |
| 22 | open position |
| 23 | closed position |
| 24 | cylindrical sidewall |
| 25 | circular bottom wall |
| 26 | opening |
| 27 | annular flexible section |
| 28 | open center |
| 29 | speed control |
| 30 | knob |

| -continued | |
| --- | --- |
| PARTS LIST | |
| Part Number | Description |
| 31 | fast position |
| 32 | medium position |
| 33 | slow position |
| 34 | indicator light |
| 35 | cover switch |
| 36 | hearing aid |
| 37 | hearing aid |
| 38 | counterweight |
| 39 | timing circuit |
| 40 | switch |
| 41 | microcontroller |
| 42 | tachometer |
| 43 | probe |
| 44 | hard wax |
| 45 | tube |
| 46 | receiver |
| 47 | receiver case |
| 48 | liquid wax |
| 49 | arrow |
| 50 | hearing aid cleaner apparatus |
| 51 | cleaning solution/solvent |
| 52 | bottle |
| 53 | needle |
| 54 | rotary chamber |
| 55 | interior |
| 56 | cylindrical wall |
| 57 | opening |
| 58 | opening |
| 59 | opening |
| 60 | opening |
| 61 | foam body |
| 62 | cylindrical section |
| 63 | cut-out |
| 64 | hearing aid |
| 65 | counterweight |
| 66 | hearing aid cleaner apparatus |
| 67 | base/motor drive |
| 68 | switch |
| 69 | cover |
| 70 | latch part |
| 71 | latch part |
| 72 | rotary chamber |
| 73 | hub |
| 74 | receptacle |
| 75 | concavity |
| 76 | hinge |
| 77 | opening |
| 78 | counterweight end portion |
| 79 | receptacle end portion |
| 80 | radially extending support |
| 81 | fastener |
| 82 | side wall |
| 83 | bottom wall |
| 84 | stop |
| 85 | space |
| 86 | slot |
| 87 | stop |
| 88 | arrow |
| 89 | arrow |
| 90 | counterweight |
| 91 | t-shaped opening |
| 92 | lower slot |
| 93 | upper slot |
| 94 | plate |
| 95 | weight |
| 96 | weight |
| 97 | user |
| 98 | position |
| 99 | position |
| 100 | position |
| 101 | position |
| 102 | opening |
| 103 | handle |
| 104 | prove |
| 105 | ell shaped end portion |

-continued

PARTS LIST

| Part Number | Description |
|---|---|
| 106 | arrow |
| 107 | fuse |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of cleaning cerumen from a hearing aid that has a receiver and a receiver tube, comprising the steps of:
    a) providing a rotary chamber having opposed ends spaced circumferentially apart, one of the ends having a receptacle, the other end having a counterweight;
    b) supporting the hearing aid in the receptacle wherein the tube is generally horizontally oriented and wherein the hearing aid is supported such that it extends through a vertical annular wall that is provided on the rotary chamber;
    c) contacting the cerumen with a solvent; and
    d) separating cerumen from the hearing aid by rotating the chamber in excess of 2200 rpms, but lower than a rotational speed that would damage the hearing aid.

2. The method of claim 1 wherein the receptacle is in the form of a wall and a wall opening and wherein in step "b" the hearing aid is at least partially supported by the wall and in step "d" cerumen is collected radially outward of the opening.

3. The method of claim 1 wherein the rotating of step "d" has a duration of between about 5 and 60 seconds.

4. The method of claim 1 wherein the rotating of step "d" has a duration of between about 18 and 22 seconds.

5. The method of claim 1 wherein the counterweight is another hearing aid.

6. The method of claim 1 wherein the solvent includes an alcohol.

7. The method of claim 1 further comprising providing a collection container that is positioned radially beyond the receptacle and collecting the cerumen with the container.

8. A method of cleaning a hearing aid comprising the steps of:
    a) providing a rotary chamber having a hearing aid receptacle;
    b) supporting the hearing aid in the receptacle, wherein the hearing aid is supported such that it extends through a vertical annular wall that is provided on the rotary chamber;
    c) counter weighing the hearing aid and receptacle;
    d) contacting the cerumen with a solvent that softens the cerumen; and
    e) separating cerumen from the hearing aid by rotating the chamber at a high rate of rotational speed of at least about 2000 rpms but at a rotational speed sufficiently low that the hearing aid is not damaged.

9. The method of claim 8 further comprising contacting the cerumen with an alcohol containing solvent before step "e".

10. The method of claim 8 wherein the solvent includes alcohol and an antimicrobial agent.

11. The method of claim 8 wherein the solvent includes an antimicrobial agent.

12. The method of claim 11 wherein the antimicrobial agent is hydrogen peroxide.

13. The method of claim 12 wherein the solvent includes alcohol and water.

14. The method of claim 8 wherein the rotating of step "e" has a duration of between about 5 and 60 seconds.

15. The method of claim 8 wherein the rotating of step "e" has a duration of between about 18 and 22 seconds.

16. The method of claim 1, wherein no heat is applied to the hearing aid as it is being rotated.

17. The method of claim 1, wherein the chamber is rotated in excess of 2800 rpms.

* * * * *